United States Patent [19]

Rink

[11] Patent Number: 4,859,736
[45] Date of Patent: Aug. 22, 1989

[54] SYNTHETIC POLYSTYRENE RESIN AND ITS USE IN SOLID PHASE PEPTIDE SYNTHESIS

[75] Inventor: Hans Rink, Riehen, Switzerland

[73] Assignee: Ciba-Geigy Corporation, Ardsley, N.Y.

[21] Appl. No.: 171,049

[22] Filed: Mar. 21, 1988

[30] Foreign Application Priority Data

Mar. 30, 1987 [CH] Switzerland ............... 1214/87

[51] Int. Cl.$^4$ ............... C08L 89/00; C07C 103/52
[52] U.S. Cl. ............... 525/54.1; 525/54.11; 530/334
[58] Field of Search ............... 525/54.1, 54.4, 333.3, 525/333.4; 526/346, 347, 347.1; 530/333, 334

[56] References Cited

U.S. PATENT DOCUMENTS 4,569,967 2/1986 Kornreich et al. ............... 525/54.11
4,731,412 3/1988 Kaiser et al. ............... 525/54.11

OTHER PUBLICATIONS

Southard et al., Tetrahedron, vol. 27, pp. 2701-2703 (1971).
Atherton et al., Proceedings of the 7th American Peptide Symposium (1981) pp. 163-175.
Rink, Tetrahedron Letters, vol. 28, No. 33, pp. 3787-3790 (1987).
Rink, Peptide Chemistry, 1987, Protein Research Foundation, Osaka (1988) pp. 279-282.
Penke et al., J. Org. Chem., vol. 52, No. 7, pp. 1197-2000 (1987).
Breipohl et al., Tetrahedron Letters, vol. 28, No. 46, pp. 5651-5654 (1987).

Primary Examiner—John Kight
Assistant Examiner—Nathan M. Nutter
Attorney, Agent, or Firm—JoAnn Villamizar; Irving M. Fishman

[57] ABSTRACT

A synthetic resin based on a polystyrene that can be used as a support for solid phase peptide synthesis and that has been cross-linked with from 0 to 5 mol % of divinyl benzene, characterized in that it has been substituted at benzene rings of its skeletal structure by groups of the formula

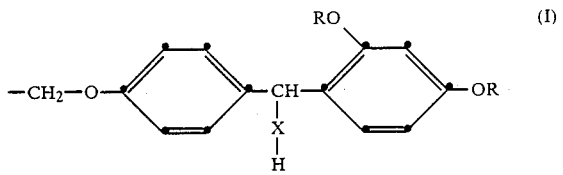

in which X represents —O— or —NH— and R represents $C_1$-$C_4$-alkyl, as a support renders possible the solid phase synthesis of peptides and peptide amides that are, if desired, protected at the N-terminal and/or at other functional groups. The resin is manufactured by reaction of a customary chloromethylated polystyrene resin with an alkali metal salt of the corresponding 4-hydroxybenzophenone and subsequent reduction of the carbonyl group and, optionally, amination.

6 Claims, No Drawings

SYNTHETIC POLYSTYRENE RESIN AND ITS USE IN SOLID PHASE PEPTIDE SYNTHESIS

The invention relates to a novel synthetic resin for use as a support for the synthesis of peptides and peptide amides in solid phase in accordance wth the known general principle of the Merrifield synthesis. The synthetic resin according to the invention consists of the skeletal structure of a polystyrene that can be used for such a Merrifield synthesis and that has optionally been cross-linked by copolymerisation with from 0 to 5 mol%, preferably from 1 to 2 mol%, of divinyl benzene and is characterised in that it has been substituted at benzene rings of its skeletal structure by groups of the formula

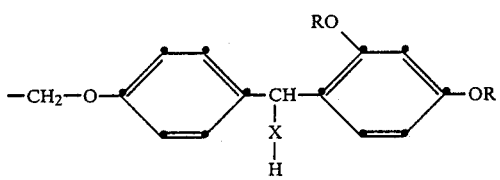 (I)

in which X represents —O— or —NH— and R represents $C_1$–$C_4$-alkyl. X in a resin according to the invention is preferably —O—, and the symbol R is preferably a linear $C_1$–$C_4$-alkyl, especialy methyl.

The invention also relates to a process for the manufacture of the above-characterised resin and to its use for the manufacture of peptides and peptide amides, especially those that are protected at the N-terminal amino group and/or at the remaining functional groups. The invention relates also to corresponding resins in which the radical —XH, when it represents —NH$_2$, is in protected form, and to resins with attached, optionally protected, amino acid, peptide and peptide amide residues, and also to the free peptides and peptide amides manufactured by the above-mentioned process, especially those described in the Examples.

The principle of the Merrifield synthesis of peptidic compounds, published in 1962, is generally known. In this process, an amino acid protected at one terminal (usually the N-terminal) is bonded (attached) to a suitably functionalised base polymer (in the most common form to a chloromethylated polystyrene). The bond should on the one hand be sufficiently strong to remain intact under the various reaction conditions of the synthetic construction of the peptide (especially the removal of the N-terminal amino-protecting group), but on the other hand should allow the finished peptide to be detached from the polymer support under conditions that do not impair the product. The actual synthesis is then carried out at the amino acid that is attached to the support; in this process usually the N-terminal protecting group is removed, the freed amino group is acylated by a suitable amino acid derivative protected at the N-terminal (that is to say a new peptidic bond is formed), and the removal of the terminal protecting group and acylation with a further amino acid residue is repeated until an amino acid sequence of the desired length is obtained. This sequence is then detached (removed) from the support as the finished peptide by means of a suitable reagent. This ideal reaction course suffers from a number of disadvantages and sources of errors when carried out in practice, and over the last 25 years peptide literature has been actively concerned with these problems. One of the most difficult problems is that the synthesised sequence on the support cannot be freed of secondary products, and a defective structure that has already been formed (for example a secondary product with a shortened sequence) co-reacts in every further stage of the synthesis and is carried over into subsequent stages so that, at the end, the desired product is often obtained only in a small quantity together with a predominant mass of secondary products of similar structure from which it has to be separated in a complicated manner. This situation is especially difficult if the amino acids used contain other side chain functional groups that must virtually always be protected (owing to the relatively energetic conditions in the acylation operation). These protecting groups, in turn, must be sufficiently resistant to remain intact when the N-terminal amino group is freed. Yet another problem is posed by peptide amides since their bond to the support (in contrast to the ester bond of conventional peptides), is also a peptidic bond like the bond between amino acids of the complete amino acid sequence. The difficulty therefore arises of selectively detaching a peptide amide from the support whilst retaining the other peptidic bonds. For these (and also other) reasons, solid phase synthesis (Merrifield synthesis) is currently regarded as a method having certain advantages only when synthesising peptides having a maximum of 30 amino acids.

In order to broaden its field of application, it has been proposed, see, for example, E. Atherton et al., Proceedings of the 7th American Peptide Symposium, pages 163–195, Pierce Chemical Company, Rockford, IL, U.S.A. (1981), that entire amino acid partial sequences having protected functional groups (including the N-terminal amino group) be attached in the form of building blocks to a support and linked with other protected peptide fragments in the form of building blocks. It should, then, be possible also to produce these necessary building blocks (peptide fragments) by solid phase synthesis on a support. This, however, presents an entirely new problem. For this, a resin is required that permits the synthesised peptide fragment, which consists of several protected amino acid residues, to be released from attachment to the resin under such mild and/or selective conditions that neither the N-terminal protecting group nor the protecting groups of other functional groups (which of necessity must be different from the former) are affected. A detailed discussion of various proposals and partial solutions can be found in the above-mentioned publication of Atherton et al.; these authors have themselves proposed as their own best solution the use of a polyamide base resin that is bonded by way of norvaline to 2- or 3-methoxy-4-hydroxymethylphenoxyacetic acid. The C-terminal of the first (protected) amino acid is then attached to the hydroxymethyl group by an ester bond; the cleaving of this bond (detachment from the resin) at the end of the synthesis is effected using 1% trifluoroacetic acid in methylene chloride. But even this method, which can probably be considered as one of the best in the State of the Art, is not universally applicable since, as stated by the authors themselves, under the removal conditions at the end of the synthesis at least two very important protecting groups of the side chains, that is the tert.-butoxycarbonyl protecting group of the ε-amino group of lysine and the tert.-butyl group protecting the hydroxy group of tyrosine, are so easily removed that the use of these protecting groups becomes questionable.

Moreover, the resin is not suitable for a direct solid phase synthesis of peptide amides. All of this probably explains why this method has not been more widely used so far in spite of its clear advantages.

Surprisingly, it has now been found that the synthetic resin according to the invention is free from the known disadvantages of the earlier proposals and thus permits a wide application of the solid phase synthesis of protected and unprotected peptides and peptide amides. Preferably, the most used support polymer, that is polystyrene, is used as the polymer skeleton for the synthesis of the synthetic resin.

Practically any synthetic resin that contains phenyl groups in its skeleton can be used as the base polymer. Polymers of styrene, which have been in general use for 20 years as supports for the solid phase synthesis of peptides and which are available in the form of various commercial preparations for that purpose, are preferred. In order to increase the stability and insolubility in organic solvents, polystyrene resins that have been cross-linked by copolymerisation with at most 5 mol%, and preferably approximately from 1 to 2 mol%, divinyl benzene, are preferred. Such base polymers are substituted at their phenyl groups (benzene rings) by chloromethylation or bromomethylation and then the actual anchor groups are introduced at the methylene group by exchanging chlorine or bromine, respectively. Also, halomethylated, especially chloromethylated, polysytrene resins are common commercial products which, under the name "Merrifield resin", are widely used in the solid phase synthesis of peptides.

The process according to the invention for the manufacture of the above-defined novel synthetic resins comprises reacting a suitable polystyrene, for example an above-described polystyrene cross-linked with from 0 to 5 mol% divinyl benzene and chloromethylated or bromomethylated at benzene rings of the skeletal structure, in succession, (a) with a compound of formula

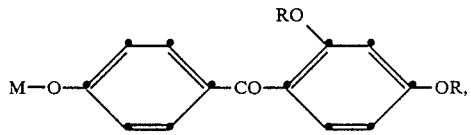

in which M is an alkali metal and R has the meaning given above, (b) with a reducing agent and, if X represents —NH—, (c) with a reagent that introduces the amino group.

The reaction according to process step (a) is carried out in the presence of a highly polar solvent that preferably has a good dissolving capacity for salts, for example a dipolar aprotic solvent, such as dimethyl sulphoxide, acetonitrile, hexamethylphosphorus triamide, N,N'-propylene urea or an aliphatic amide, such as, especially, dimethylformamide, or also mixtures of the mentioned solvents and, preferably, with the strict exclusion of moisture. Preferably a solution of the alkali metal salt of formula II is used; a caesium salt (M is caesium) is especially suitable for that purpose. The reaction can be carried out at temperatures of from 0° to 50° C., preferably in the region of room temperature, the reaction times accordingly extending to several, for example from 8 to 72, hours. During that time, the reaction mixture is preferably stirred or shaken mechanically. The 2,4-dialkoxy-4'-hydroxybenzophenones used as starting material can be obtained in a manner known per se, for example by C-acylation of a corresponding resorcinol diether with p-hydroxybenzoyl chloride catalysed by aluminium chloride, or by a modification of this acylation; the desired salt is obtained therefrom by conventional reaction with the corresponding alkali metal hydroxide, such as caesium hydroxide.

Process step (b) is carried out in a manner known per se by reaction with a reducing agent, for example one that is customary for reducing oxo groups to hydroxy groups. Suitable reducing agents are, for example, diborane or complex hydrides, such as, especially, alkali metal borohydrides (for example sodium borohydride, lithium borohydride or potassium borohydride) as well as, also, alkali metal aluminium hydrides (for example sodium aluminium hydride or lithium aluminium hydride), which are used in expedient non-reactive organic solvents, especially open-chained or cyclic ethers (for example diisopropyl ether or 1,2-dimethoxy- or -diethoxy-ethane, or dioxan or tetrahydrofuran, respectively) at temperatures of from 0° to approximately 100° C., depending on the reagent. The reaction times depend on the reagents and reaction conditions employed and as a rule range from 1 to 48 hours; shaking or stirring facilitates contact between the solid and liquid components. If necessary, the reduction process can be repeated with a fresh amount of reducing agent; excess reagent is advantageously destroyed at the end of the reaction, for example by a ketone, such as acetone.

The optional process step (c), which is used to convert the "hydroxy resin" obtained in accordance with (b) into the "amino resin", is carried out, for example, with ammonia. For this purpose, for example ammonia gas is introduced into a stirred suspension of the "hydroxy resin" in a polar solvent, for example one of the solvents mentioned in process step (a) or (b), at temperatures of from 0° C. to room temperature; this process can especially also be carried out under elevated pressure at temperatures of up to 50° C. with shaking.

Carbamates from which the alcohol moiety can be removed by treatment with a base but which are stable under acidic reaction conditions are especially suitable as the reagents for introducing the amino group used in process step (c). Examples of such carbamates are substituted ethylcarbamates that carry activating, especially electron-attracting, substituents in the β-position. The following are suitable: β-(lower alkane- or arenesulphonyl)-ethylcarbamates, for example 62 -(methanesulphonyl)-ethylcarbamate or β-(benzenesulphonyl)-ethylcarbamate, β-(nitro-, cyano- or halophenyl)-ethylcarbamates, for example 62 -(p-nitrophenyl)-ethylcarbamate, β-di-(p-nitrophenyl)-ethylcarbamate or β-(pentafluorophenyl)-ethylcarbamate, or especially 9-fluorenylmethylcarbamate. In the reaction with the above-mentioned carbamates a suspension of the "hydroxy resin" in an inert organic solvent, for example a halohydrocarbon, such as methylene chloride, chloroform or 1,2-dichloroethane, or an ether, such as diisopropyl ether, diisobutyl ether, dimethoxyethane, diethoxyethane, tetrahydrofuran or dioxan, is stirred at temperatures of from 20° to 80° C., preferably of approximately 50° C., with the carbamate and a strong acid, for example an organic sulphonic acid, preferably a lower alkanesulphonic or arenesulphonic acid, for example methanesulphonic acid, benzenesulphonic acid or p-toluenesulphonic acid, for a few hours, for example from 2 to 48 hours. In this manner a synthetic resin of the above-defined structure is obtained that carries instead of the —X—H group a —NH—W group in which W represents an amino-protecting group that can be removed by treatment with a base, especially a substituted ethoxycarbonyl group. To free the "amino resin" the protecting group is then removed with a base, for example with a solution of a tertiary or, preferably, secondary, open-chained or cyclic amine, for example triethylamine, tributylamine, diethylamine, piperidine, pyrrolidine or morpholine, in an inert organic solvent, preferably in one of the above-mentioned ethers or in a di-lower alkylamide, for example dimethylformamide or dimethylacetamide, at temperatures of from 0° to 50° C., preferably at approximately room temperature, with reaction times of from a few minutes, for example 1 minute, to a few hours, for example 6 hours. It is also possible to use an alkali metal hydroxide, for example sodium hydroxide, or an ammonium hydroxide, for example benzyltrimethylammonium hydroxide, instead of an amine, in which case, even at lower temperatures, the cleaving is already concluded after shorter reaction times, for example after less than 1 minute.

As already mentioned hereinbefore, the invention also relates to the use of the synthetic resin according to the invention as a support for the solid phase syhthesis of peptides and peptide amides, especially those that are protected at the N-terminal amino group and/or at functional groups of the side chains.

In accordance with the invention, the peptidic compounds are manufactured using the above-defined synthetic resin as follows:

(a) the synthetic resin is reacted with a compound of formula $W^1$—$AM^1$—Y—H in which Y represents —O— or —NH—, $W^1$ represents an N-terminal amino-protecting group and $AM^1$ represents the acyl radical of an amino acid sequence consisting of from 1 to 25 amino acid residues which is, if desired, protected at functional groups, or with a reactive functional derivative thereof, for the purpose of attaching the residue $W^1$—$AM^1$— to the —X— group of the resin, (b) the N-terminal protecting group $W^1$ is removed, (c) the freed N-terminal amino group is acylated by reaction with an acid of formula $W^2$—$AM^2$—OH in which $W^2$ and $AM^2$ have meanings analogous to those of the above-defined radicals $W^1$ and $AM^1$, or with a reactive functional derivative thereof, (d) the operation of alternate removal according to (b) and acylation according to (c) is repeated as required until the desired amino acid sequence is obtained and (e) the resulting peptide or peptide amide, if desired after the removal or simultaneously with the removal of protecting groups, is removed from the resin by acidolysis.

When attaching the C-terminal protected amino acid or amino acid sequence to the resin of the invention, the conditions are always chosen taking into account the reacting functional groups concerned. The support resin preferably used is the "hydroxy resin" of formula I in which X represents —O—; if the end product is desired in the amide form, that resin can be reacted with a protected amino acid amide or with a protected amino acid sequence that is in the form of an amide, for example with a compound of formula $W^1$—$AM^1$—$NH_2$ in which $W^1$ and $AM^1$ are as defined above, in which reaction the hydroxy groups —XH of the resin are exchanged for the amidic C-terminal amino group. The attchment is usually acid-catalysed, for example by means of an organic sulphonic acid, preferably a lower alkanesulphonic or an arenesulphonic acid, for example methanesulphonic acid, benzenesulphonic acid or p-toluenesulphonic acid, and carried out in the presence of inert organic solvents, such as chlorinated alkanes (for example methylene chloride, chloroform or 1,2-dichloroethane) and/or open-chained or cyclic ethers (for example diethyl, diisopropyl or dibutyl ether, or 1,2-dimethoxy- or 1,2-diethoxyethane, or dioxan or tetrahydrofuran, respectively) for several, for example from 2 to 48 hours at temperatures of from 20° to 80° C., preferably at approximately 50° C. If necessary the attachment operation can be repeated. The resin with attached C-terminal amide, that is to say one in which the benzene rings have been substituted by radicals of the formula

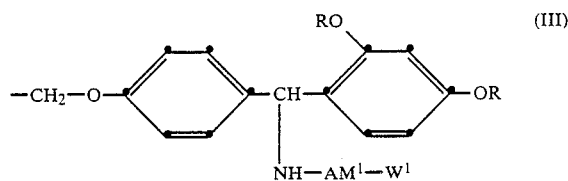

in which R, $W^1$ and $AM^1$ have the meanings given above, is then subjected to the synthesis of the desired amino acid sequence in accordance with process steps (b) to (d). The detachment of the finished peptide amide (process step e) can be carried out with hydrogen fluoride, but is preferably carried out with milder acidic agents, such as trifluoroacetic acid, preferably in an inert organic diluent, such as a haloalkane, or in water. For example, the detachment is carried out using a mixture of trifluoroacetic acid and methylene chloride or 1,2-dichloroethane, for example in a ratio by volume of 1:1. However, not all of the acidolytically removable protecting groups customarily used are resistant under these conditions. Depending on the reaction procedure, therefore, at the same time as the detachment from the resin the corresponding protecting groups are also removed, resulting in a peptide amide having free functional groups.

If the peptide at the end of the synthesis is desired in the form of a free acid (if desired with an N-terminal protecting group and/or other protecting groups), then the support resin used is again the "hydroxy resin" of formula I in which X represents —O—. This is reacted with a protected amino acid or with a protected amino acid sequence in the form of the free acid or in the form of a reactive functional derivative of the acid, for example with a compound of formula $W^1$—$AM^1$—OH in which $W^1$ and $AM^1$ are as defined hereinbefore, in which reaction the hydroxyl group of the resin is esterified. The attachment reaction is carried out under acylation conditions customary in peptide synthesis. The reactive functional derivative used is, for example, an anhydride of the acid to be attached, especially a symmetrical anhydride, preferably in the presence of organic tertiary bases, suchas those mentioned hereinafter. Another suitable functional derivative is an active ester of the acid to be attached, which is also reacted in the presence of the organic tertiary bases mentioned hereinafter. Suitable active esters are especially esters of phenols that carry electron-attracting substituents, and esters of N-hydroxyimides. Preferably, however, the compound to be attached is used in the form of the free acid and is acylated with the aid of carbodiimides, for example diisopropylcarbodiimide or especially dicyclohexylcarbodiimide, as condensation agent. The reaction is carried out in the presence of organic bases, especially tertiary bases (such as pyridine, quinoline, 4-dimethylaminopyridine, N-methylpiperidine, N-methylmorpholine, N,N'-dimethylpiperazine, or triethylamine or diisopropylethylamine) and in inert organic solvents, such as chlorinated alkanes (for example methylene chloride or chloroform) and/or open-chained or cyclic ethers (for example diethyl, diisopropyl or dibutyl ether, or 1,2-dimethoxy- or 1,2-diethoxy-ethane, or dioxan or tetrahydrofuran, respectively). An activated N-hydroxy compound, for example 1-hydroxybenzotriazole, is preferably added. The reaction time is as a rule several, such as from 2 to 48, hours at temperatures of from 0° to 40° C.; if desired the acylation process can be repeated. As a means of avoiding undesired secondary products it is advantageous to treat the resulting resin with benzoyl chloride (or a similar simple acid derivative) in the presence of a base, such as one of those mentioned hereinbefore, and thus block the hydroxy groups of the resin which may still be free. The resin with attached C-terminal ester, that is to say one in which the benzene rings have been substituted by radicals of formula

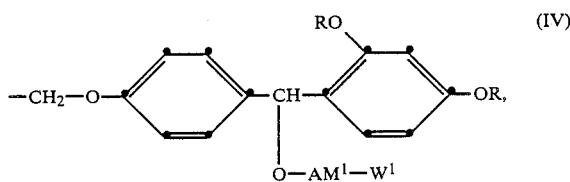

in which R, $W^1$ and $AM^1$ have the meanings given hereinbefore, is then subjected to the synthesis of the desired amino acid sequence in accordance with process steps (b) to (d). If an end product without protecting groups, especially without acid-labile protecting groups, is desired, the detachment of the finished peptide acid (process step e) can be carried out with hydrogen fluoride, but is preferably carried out with milder acidic agents, such as trifluoroacetic acid, which is preferably diluted with an inert organic solvent, such as a haloalkane. If a peptide (amino acid sequence) is desired in which the N-terminal amino group and/or the other functional groups are retained in protected form, as is usually desirable in the case of peptide fragments that are to be used for further synthesis, the detachment of the end product from the resin is carried out under especially mild acidolytic conditions, for example with an organic acid, especially a lower alkanecarboxylic acid, preferably formic or propionic acid or, more especially, acetic acid, which may be diluted with neutral organic solvents, for example chlorinated alkanes or aliphatic or cyclic ethers; there may be mentioned as being especially advantageous, for example, a mixture of acetic acid and methylene chloride or chloroform in a ratio by volume of from approximately 1:1 to approximately 1:19, especially of 1:9. Also suitable are highly diluted trifluoroacetic acid, for example in the form of a 0.1 to 2% solution in methylene chloride or chloroform, or a pyridinium salt, for example pyridinium hydrochloride, in a polar, salt- and peptide-dissolving solvent, for example in dimethylacetamide or dimethylformamide. The detachment is usually carried out in a temperature range of from 0° to 50° C., preferably in the region of room temperature, the reaction time extending from a few minutes to several (for example from 2 to 8) hours.

It is also possible to obtain peptide amides using as the support resin the "amino resin" of formula I in which X represents —NH— and reacting it with a protected amino acid or protected amino acid sequence in the form of the free acid or in the form of a reactive functional derivative of the acid, for example with a compound of formula $W^1$—$AM^1$—OH in which $W^1$ and $AM^1$ are as defined hereinbefore. This results in a resin with an attached C-terminal amide, that is to say a resin in which the benzene rings have been substituted by radicals of formula III. The reaction is preferably carried out under the reaction conditions mentioned above for the esterification of the "hydroxy resin" with free acid or a reactive functional derivative thereof. The synthesis of the desired amino acid sequence according to the process steps (b) to (d) and the detachment of the finished peptide amide according to process step (e) are then carried out exactly as described hereinbefore.

The relative ease with which the amino acid sequence can be detached from the resin is determined by the special choice of the N-terminal amino-protecting group, the removal of which must be strictly selective, with the sequence remaining attached to the resin (and also with the retention of other protecting groups), but nevertheless quantitative. This N-terminal amino-protecting group $W^1$ or $W^2$ is preferably a group that can be removed under basic conditions, especially a group of the oxycarbonyl type. Preferred N-terminal amino-protecting groups $W^1$ and $W^2$ are substituted ethoxycarbonyl groups that carry in the β-position activating, especially electron-attracting, substituents, such as those mentioned hereinbefore in the case of the corresponding carbamates. Especially suitable are the β-(methanesulphonyl)-ethoxycarbonyl group, the β-(p-nitrophenyl)-ethoxycarbonyl group and the β-di-(p-nitrophenyl)-ethoxycarbonyl group, and more especially the 9-fluorenylmethoxycarbonyl group (Fmoc). These protecting groups can be removed with inorganic or organic bases, especially with tertiary or secondary amines, such as those mentioned hereinbefore for the manufacture of the "amino resin". The conditions for the removal of the N-terminal amino-protecting group in accordance with process step (b), especially of the Fmoc group, are described hereinbefore in connection with the manufacture of the "amino resin" and are generally known.

The acylation of the freed N-terminal amino group in accordance with process step (c) is carried out under generally customary conditions that are common for solid phase synthesis, especially on a Merrifield support. Of the numerous known variants, attention is drawn in particular to that in which the acylation is carried out with an amino acid (or amino acid sequence) protected at the N-terminal by Fmoc or by an equivalent base-labile protecting group, in which all the functional groups of the side chain are in protected form, or with a reactive functional derivative of that acid, for example the symmetrical anhydride or an active ester. If the free acid is used, then the condensation agent employed is dicyclohexylcarbodiimide (or an analogous reagent), preferably in combination with 1-hydroxybenzotriazole, and in the presence of tertiary organic bases, for exammple tertiary aliphatic or cyclic amines or heteroaromatic bases, such as triethylamine, diisopropylethylamine, N,N-dimethylaniline, N-methylpiperidine, N-ethylpiperidine, N-methylmorpholine, N,N'-dimethylpiperazine, or pyridine and homologues thereof, quinoline or 4-dimethylaminopyridine. The acylation with the symmetrical anhydride or the active ester is also carried out in the presence of the mentioned tertiary bases and preferably also in the presence of 1-hydroxybenzotriazole. Suitable active esters are esters with phenols that carry electron-attracting substituents, for example p-nitrophenol, pentafluorophenol or 2,4,5-trichlorophenol, or with N-hydroxyimides, for example with N-hydroxysuccinimide or N-hydroxy-norbornane- or 5-norbornene-2,3-dicarboxylic acid imide. The acylation conditions of the mentioned variants are generally known; if desired, the acylation process can be repeated and/or, in order to prevent the formation of incorrect sequences, the residual non-acylated starting material can be acylated in a conventional manner with a simple carboxylic acid derivative, such as acetic anhydride or acetyl chloride, and thus blocked from further undesired acylations by amino acid residues in later stages of the synthesis.

Suitable amino acid residues for the synthesis according to the invention are those derived from naturally occurring α-amino acids of the L-series especially in the form of peptide building blocks, and closely related analogues thereof, such as, especially, the enantiomers of the "unnatural" D-series. Preferred α-amino acids are, for example, glycine, alanine, valine, leucine, isoleucine, phenylalanine, aspartic acid, glutamic acid, arginine, histidine and lysine, and also α-aminobutyric acid, norvaline, isovaline, norleucine, ornithine and citrulline, as well as asparagine, glutamine, tyrosine, tryptophan, methionine, threonine, serine, but also proline and hydroxyproline (in which the α-amino group is combined with the alkyl radical to form a ring), and also cysteine and cystine (the latter occurring as a pair of 2 cysteine residues bonded together, which may also be located at positions of the sequence separated from one another). Also suitable are residues of other amino acids that are derived from $C_1$-$C_7$-alkanecarboxylic acids, especially linear ones, and that carry the amino group in any position of the chain, for example at the terminal C-atom (such as in β-alanine, γ-aminobutyric acid or δ-aminovaleric acid); in addition they may also carry other primary amino groups (as in α,γ-diaminobutyric acid) or be substituted by other functional groups, such as hydroxy, mercapto, disulphido, guanidino, carboxy or carboxamide groups, or by cyclic hydrocarbyl or heterocyclyl radicals, such as phenyl, p-hydroxphenyl, indolyl or imidazolyl. If they contain asymmetric C-atoms these amino acids may be used in racemic form or, preferably, in optically active form.

The specific character of the solid phase synthesis demands that functional groups in the amino acid residues used that do not participate in the reaction (and also those that can remain free in liquid phase syntheses) are as a rule in protected form.

The choice of protecting groups depends on the conditions of the synthesis and on the use of the end product to be produced. If several functional groups are to be protected then advantageous combinations must be selected. In particular, care should be taken that protecting groups of functional groups of the amino acid side chains are resistant during the removal of the N-terminal protecting group, such as the Fmoc group, and, if a protected peptide building block for a further synthesis is desired as end product, that they are stable under the mild acidic conditions employed for the detachment from the resin at the end of the synthesis.

To protect other amino groups present, such as the ε-amino group in the lysine residue, it is possible to use any amino-protecting group customary in peptide chemistry that is stable under weakly basic conditions. Suitable groups are described collectively in known reference works, for example in Houben-Weyl; Methoden der organischen Chemie, 4th edition, vol 15/I, E. Wünsch (editor), Synthese von Peptiden (Georg Thieme Verlag, Stuttgart, 1974).

It is thus possible to use, for example, amino-protecting groups that can be removed by reduction or under energetic basic conditions, for example especially the benzyloxycarbonyl group and benzyloxycarbonyl groups that have been substituted in the aromatic moiety by halogen atoms, nitro groups, lower alkoxy groups and/or lower alkyl radicals, such as the p-chloro- or p-bromo-benzyloxycarbonyl, p-nitrobenzyloxycarbonyl, p-methoxybenzyloxycarbonyl or p-tolylmethoxycarbonyl group, and also the isonicotinyloxycarbonyl group, as well as also sulphonyl groups such as p-toluenesulphonyl, benzenesulphonyl, o-nitrobenzenesulphonyl and other substituted benzenesulphonyl groups or also acyl groups, such as formyl, trifluoroacetyl or phthaloyl. An advantageous amino-protecting group is an ethoxycarbonyl group that carries in the β-position a silyl group substituted by three hydrocarbon radicals, such as triphenylsilyl, dimethyl-tert.-butyl-silyl or, especially, trimethylsilyl. Such a β-(trihydrocarbylsilyl)-ethoxycarbonyl group, such as a β-(tri-lower alkylsilyl)-ethoxycarbonyl group, for example especially the β-(trimethylsilyl)-ethoxycarbonyl group, is resistant under the conditions of acidic hydrolysis and of hydrogenolysis, but can be removed under quite specific, very mild conditions by the action of fluoride ions. In this respect it behaves analogously to the β-silylethyl ester group described hereinafter as a carboxy-protecting group.

More especially preferred are groups that can be removed by acidolysis, such as, especially, tert.-butoxycarbonyl and analogous groups, for example the tert.-amyloxycarbonyl, isopropoxycarbonyl, diisopropylmethoxycarbonyl, allyloxycarbonyl, cyclopentyloxycarbonyl, cyclohexyloxycarbonyl, d-isobornyloxycarbonyl and adamantyloxycarbonyl groups, and also groups of the aralkyl type, such as benzhydryl and triphenylmethyl (trityl), and also aralkoxycarbonyl groups of the 2-aryl-2-propoxycarbonyl type, for example the 2-phenyl- or 2-p-biphenylyl-2-propoxycarbonyl groups.

It is possible for one of the above-mentioned amino-protecting groups to be used as a protecting group of the guanidino function, as occurs, for example, in the natural amino acid arginine. Especially suitable are sulphonyl groups, especially lower alkanesulphonyl, for example methane-, ethane- or isopropane-sulphonyl groups, or arenesulphonyl, for example substituted benzenesulphonyl, groups, suitable substituents being lower alkyl, for example methyl, lower alkoxy, fpr example methoxy, fused lower alkoxy, for example 1-oxa-1,4-butylene, nitro or halogen, for example chlorine or bromine. The 2,3,5-trimethyl-4-methoxybenzenesulphonyl group and the 2,2,5,7,8-pentamethyl-chroman-6-sulphonyl group are especially preferred.

It is possible to use a hydroxy-protecting group any group customary in peptide chemistry for that purpose, cf. the above-cited review in Houben-Weyl. Groups that can be removed by acidolysis, such as 2-tetrahydropyranyl and more especially tert.-butyl, as well as, also, tert.-butoxycarbonyl, are preferred. It is also possible, however, to use hydroxy-protecting groups that can be removed by reduction or under basic conditions, for example benzyl or benzyloxycarbonyl groups which may be substituted in the aromatic moiety by halogen, nitro and/or by lower alkoxy, lower alkanoyl radicals, such as acetyl, or aroyl radicals, such as benzoyl.

It is possible to use as a carboxy-protecting group any group customary for that purpose, cf. the above-cited review in Houben-Weyl. Thus, carboxy groups are protected, for example, by hydrazide formation or by esterification. The following, for example, are suitable for the esterification: lower, optionally substituted alkanols, such as methanol, ethanol, cyanomethyl alcohol, 2,2,2-trichloroethanol, benzoylmethyl alcohol or, especially, tert.-butyl alcohol, but also an optionally substituted benzyl alcohol. An especially advantageous category of substituted alkanols are ethanols carrying a trisubstituted silyl group, such as triphenylsilyl, dimethyl-tert.-butyl-silyl or, especially, trimethylsilyl, in the β-position. These alcohols are especially suitable for the protection of carboxy groups because the corresponding β-silylethyl esters, for example β-(trimethylsilyl)ethyl ester, do indeed have the stability of customary alkyl esters, but can be removed selectively with fluoride ions whilst all other protecting groups are retained.

There may be used as a mercapto-protecting group any group customary in peptide chemistry for that purpose. The mercapto groups are protected especially by suitable acylation or alkylation. The following, for example, are suitable for the acylation: the acetyl or benzoyl radical, a lower alkyl- (for example ethyl-) carbamoyl group, or a benzyloxycarbonyl group optionally substituted as indicated hereinbefore. The following, for example, are suitable for the alkylation: the tert.-butyl, isobutoxymethyl, benzylthiomethyl or tetrahydropyranyl radical, or arylmethyl radicals optionally substituted by halogen, lower alkoxy or by nitro, such as benzyl, p-methoxybenzyl, diphenylmethyl, dimethoxybenzhydryl or, more especially, trityl, as well as, also, phenylcyclohexyl, p-methoxyphenylcyclohexyl, or 2-thienylcyclohexyl. An acylaminomethyl radical in which acyl is, for example, acetyl or alternatively benzoyl, is also very advantageous. The acetylaminomethyl group is especially preferred.

Preferably, the protecting groups of the side chains are so selected that they can all be removed under similar conditions; especially preferred are the groups to which attention has already been drawn that can be removed by acidolysis, especially those derived from tert.-butyl. The removal of all of these protecting groups is then advantageously carried out in a single operation.

The protecting groups are removed in generally known manner. The acidolysis or acidic hydrolysis is carried out, for example, by means of trifluoroacetic acid, hydrochloric acid or hydrogen fluoride, and in the case of readily removable protecting groups also by means of a lower aliphatic carboxylic acid, such as formic acid and/or acetic acid, in the presence of a halogenated hydrocarbon, for example methylene chloride, or of water and optionally a polyhalogenated lower alkanol or lower alkanone, such as 1,1,1,3,3,3-hexafluoropropan-2-ol or hexafluoroacetone. The groups that can be removed by reduction, especially those that contain benzyl radicals, are removed preferably by hydrogenolysis, for example by hydrogenation catalysed by palladium. The isonicotinyloxycarbonyl group is preferably removed by zinc reduction. The β-silylethoxycarbonyl group is cleaved by fluoride ions.

The invention relates also to the intermediates and end products of the synthesis process using the resin according to the invention. The invention relates especially to a synthetic resin of the structure defined at the beginning that instead of the —X—H group carries an —NH—W, —X—AM—W or —X—AM—H group in which —X— represents —O— or —NH—, W represents an N-terminal amino-protecting group and AM represents the acyl radical of an amino acid sequence consisting of from 1 to 180 amino acid residues which, if desired, is protected at functional groups, especially one of the compounds described in the following Examples. The invention relates also to peptides and peptide amides of formula W—AM$^o$—XH in which —X— represents —O— or —NH—, W represents a terminal amino-protecting group and AM$^o$ represents the acyl radical of an amino acid sequence consisting of from 2 to 180 amino acid residues which, if desired, is protected at functional groups, and to analogous compounds having a free N-terminal amino group of formula H—AM$^o$—XH, insofar as they can be obtained by the synthesis process according to the invention, especially to the peptides and peptide amides described in the following Examples.

The abbreviations used, for example for the designation of amino acids, peptides and protecting groups etc., are customary abbreviations, for example the abbreviations compiled in the above-cited review in Houben-Weyl. Unless stated otherwise, the names and abbreviations of amino acid residues refer to residues of α-amino acids of the naturally occurring L-series. Unless indicated to the contrary, the term "lower" when used in connection with an organic radical or compound indicates such a radical or compound having a maximum of 7, but preferably a maximum of 4, carbon atoms.

In the following Examples the invention is illustrated further without the scope thereof being limited in any way. The abbreviations used have the following meanings:

Boc—tert.-butoxycarbonyl
But—tert.-butyl (in ether)
TLC—thin layer chromatography
DCCI—dicyclohexylcarbodiimide
DMA—dimethylacetamide
DMF—dimethylformamide
DMSO—dimethyl sulphoxide
EDC—1,2-ethane dichloride
FAB-MS—Fast Atom Bombardment Mass Spectrum
Fmoc—9-fluorenylmethoxycarbonyl
HOBt—1-hydroxybenzotriazole
HPLC—high pressure liquid chromatography
IGF-2—Insulin-like Growth Factor-2
MIF—Macrophage migration Inhibition Factor
Mtr—2,3,5-trimethyl-4-methoxybenzenesulphonyl
OBut—tert.-butyl (in ether)
TFA—trifluoroacetic acid
THF—tetrahydrofuran
Trt—trityl

EXAMPLE 1

2,4-dimethoxy-4'-hydroxy-benzophenone (1)

The title compound is synthesised analogously to the preparation of 2,4'-dihydroxy-4-methoxy-benzophenone, see Ray, S., Grover, P. K. and Anand Nitya: Indian Journal of Chemistry 9, 619–623 (1971), from resorcinol dimethyl ether and 4-hydroxybenzoic acid. Elemental analysis, $^1$H-NMR spectrum and IR spectrum confirm the structure of (1).

EXAMPLE 2

Caesium salt of 2,4-dimethoxy-4'-hydroxybenzophenone (1A)

5.00 g of (1) (19.3 mmol) are suspended in 40 ml of ethanol and 16 ml of water and a solution of 3.25 g (19 mmol) of caesium hydroxide monohydrate in 4.5 ml of water is added. The solution is concentrated in vacuo, taken up in 40 ml of water/tert.-butyl alcohol (1:1) and lyophilised. The slightly yellowish lyophilisate, when crystallised from 20 ml of tert.-butyl alcohol, yields the salt (1A) in the form of a white powder.

EXAMPLE 3

4-(2,4-dimethoxybenzoyl)-phenoxymethyl-polystyrene (1% DVB cross-linked) (2)

20.0 g of chloromethyl-polysytrene-1% divinylbenzene (DVB) (=Merrifield polymer Fluka, Switzerland; 0.67 mmol Cl/g) (13.4 mmol) are dried under a high vacuum for 1 hour at 50° C. 26.1 g of (1A) (67 mmol) are suspended three times, with approximately 500 ml of pyridine each time, followed by concentration by evaporation under a high vacuum, and the residue is dissolved in approximately 700 ml of dry DMF and concentrated to approximately 400 ml under a high vacuum. The resin is added and the reaction mixture is shaken at room temperature for 20 hours with the exclusion of moisture. The resin is filtered and washed with 100 ml portions of the following solvents: 3×isopropyl alcohol, 3×DMF, 3×water, 3×DMF, 5×water, 4×isopropyl alcohol. The resin is dried under a high vacuum at from 40° to 45° C. until constant mass is reached. The IR spectrum exhibits the expected C=O band.

EXAMPLE 4

4-(2,4-dimethoxyphenyl-hydroxy-methyl)-phenoxymethyl-polystyrene [dimethoxybenzhydryloxymethyl-polystyrene, "hydroxy resin"] (3)

14.5 ml of 1M lithium borohydride in THF are added to a suspension of 7.07 g of (2) (approximately 4.8 mmol ketone function) in 50 ml of dry tetrahydrofuran (THF) and the reaction mixture is refluxed for 1 hour with the exclusion of moisture. After the mixture has been cooled to approximately from 0° to 5° C., 24 ml of methanol and, dropwise while stirring well, approximately 6 ml of acetone, are added. The filtered resin is washed as follows using 30 ml portions of solvent: 3×methanol, 1×water, 1×aqueous hydrochloric acid of pH approximately 3.0, 2×water, 4×methanol. The resin is dried under a high vacuum at from 40° to 45° C. until constant mass is reached. Elemental analysis: 3.67% O=2.31 mmol O/g, IR spectrum: no C=O band.

EXAMPLE 5

N-[Fmoc-Pro]-4-(2,4-dimethoxyphenyl-amino-methyl)-phenoxymethylpolystyrene [Fmoc-Pro-amino resin] (4)

A mixture of 0.46 g of (3) (approximately 0.26 mmol), 0.31 g of Fmoc-Pro-NH$_2$ (0.92 mmol), 76.5 μl of 1M benzenesulphonic acid solution in dichloromethane (76.5 μmol) and 10 ml of dioxan is stirred for 3 hours and, after the addition of a further 76.5 μl of 1M benzenesulphonic acid solution, is stirred for a further 20 hours at 50° C. The resin is filtered and washed as follows, using 5 ml portions of solvent: 5×methanol, 12×dichloromethane, 3×methanol, 3×dichloromethane. The resin is dried under a high vacuum at from 40° to 45° C. until constant mass is reached.

Using a sample weighing approximately 20 mg, the Fmoc group is removed by 4×2 minute treatments with 300 μl of 20% piperidine each time and washing six times with dimethylacetamide (DMA). The spectrophotometric determination (300 nm) gives a specific loading of 0.23 mmol of Fmoc/g of resin.

EXAMPLE 6

N-[Boc-Pro-Glu(OBut)-Ile-Pro]-amino resin (5)

0.42 g of (4) (97 μmol) is reacted to form (5) in an automatic peptide synthesiser by means of the following process by successive alternate removal of the Fmoc group and condensing (coupling) with Fmoc-Ile, Fmoc-Glu(OBut) and Boc-Pro, in each case with unreacted amino groups being blocked by acetylation.

Individual operations:

Washing and removal (deblocking) of Fmoc at room temperature with in each case approximately 10 ml: 1×isopropyl alcohol (1 min.), 4×DMA degassed (0.5 min.), 1×isopropyl alcohol (1 min.), 3×DMA degassed (0.5 min.), 4×20% piperidine in DMA (2 mins.), 2×water/dioxan (1:1) (1 min.), 5×DMA degassed (0.5 min.), 3×DMA dist. (0.5 min.).

Coupling: 0.39 mmol of N-protected amino acid, 0.68 ml of 0.57M 1-hydroxybenzotriazole (HOBt) in DMA (0.39 mmol) and 0.18 ml of 2.4M dicyclohexylcarbodiimide (DCCI) in DMA with the addition of 0.20 ml of DMA (20 mins. at room temperature, 2 hours at 40°).

Washing and acetylation of the remaining free amino groups with: 1×acetic anhydride/pyridine/DMA (1:1:8 vol.) (5 mins.), 3×DMA degassed, 1×isopropyl alcohol (1 min.), 3×DMA degassed (0.5 min.). The resin is washed with isopropyl alcohol (3×5 ml) and dried at room temperature under a high vacuum.

EXAMPLE 7

H-Pro-Glu-Ile-Pro-NH$_2$ 0.46 g of (5) (approximately 90 μmol) are stirred at room temperature for 15 minutes in trifluoroacetic acid/dichloromethane (1:1 vol.) and the resin is filtered off and washed 3 times with approximately 10 ml of dichloromethane each time. The filtrate is concentrated in vacuo to approximately 2 ml and, while stirring, is introduced dropwise into 10 ml of ether. The precipitate is filtered off and dried in vacuo. According to thin layer chromatography and HPLC the resulting colourless powder is identical to authentic tetrapeptide amide produced in solution.

EXAMPLE 8

O-[Fmoc-Gly]-hydroxy resin (6)

2.0 g of (3) (approximately 1 mmol), 1.19 g of Fmoc-Gly-OH (4 mmol) and 0.87 g of DCCI (4.2 mmol) are stirred for 5 minutes at from 0° to 5° C. in 20 ml of 1,2-ethane dichloride (EDC), 24 mg of 4-dimethylaminopyridine (DMAP) (0.2 mmol) are added and, after a further 20 minutes at approximately 5° C., 110 μl of N-methylmorpholine (1 mmol) are added. The mixture is stirred at room temperature for 4 hours. The filtered resin is washed in a peptide synthesiser with 20 ml each time of the following solvents: 3×methanol, 3×EDC, 3×DMA, in each case for 0.5 minutes. To block hydroxy groups still present in the resin, the latter is stirred at room temperature for 2 hours with 1.23 g of benzoic acid anhydride (5.4 mmol) in 1.2 ml of pyridine and 6 ml of DMA and then washed as follows, each time with 20 ml: 2×isopropyl alcohol, 3×DMA degassed, 2×isopropyl alcohol, 6×EDC, 2×isopropyl alcohol, 3×DMA degassed, 3×isopropyl alcohol, in each case for 0.5 minutes. The title compound (6), dried at 45° C. under a high vacuum, has a Fmoc content of 0.26 mmol/g.

EXAMPLE 9

O-[Fmoc-$\beta$-Ala]-hydroxy resin (7)

The title compound (7) is manufactured analogously to (6) and has an Fmoc content of 0.33 mmol/g.

EXAMPLE 10

O-[Fmoc-Leu-Pro-Glu(OBut)-Gly-Ser(But)-Pro-Val-Thr(But)-Leu-Asp(OBut)-Leu-Arg(Mtr)-Tyr(But)-Asn-Arg(Mtr)-Val-Arg(Mtr)-Val-$\beta$-Ala]-hydroxy resin (side chain-protected eglin fragment-[$\beta$-Ala$^{55}$]-eglin C(37–55)-nonadecapeptide bonded to hydroxy resin), (8)

1.10 g of (7) (0.36 mmol) from Example 9 are reacted in a peptide synthesiser with washing processes and Fmoc removal processes analogously to Example 6. Amino acids 10 to 18 (that is 46 to 54 of eglin C) are coupled in the form of 2,4,5-trichlorophenyl ester (1.08 mmol) in 1.8 ml of DMA, with the addition of 1.89 ml of 0.57M HOBt (1.08 mmol) and 0.285M diisopropylethylamine (0.54 mmol) in DMA, for two hours at room temperature. This process is repeated for amino acids 11, 12, 16 and 18 (that is 47, 48, 52 and 54 eglin C). Amino acids 1 to 9 (that is 37 to 45 of eglin C) are used for the coupling in the form of symmetrical anhydrides (1.08 mmol): 2.16 mmol of Fmoc-amino acid are dissolved in 10 ml of dichloromethane (in the case of Fmoc-Gly-OH with the addition of 1 ml of DMA), 245 mg of DCCI (1.12 mmol) are added at room temperature while stirring, the whole is maintained at room temperature for 15 minutes, the precipitated dicyclohexylurea is filtered off, 2.5 ml of DMA (distilled) are added to the filtrate and the dichloromethane is removed in vacuo. This mixture is added in each case to the synthetic resin and, after the addition of 58 $\mu$l of diisopropylethylamine (0.36 mmol), maintained at room temperature for 1 hour. When the synthesis is complete and the terminal Fmoc group has been removed in the manner described in Example 5, the resin is washed 3 times with 5 ml of isopropyl alcohol each time and dried at room temperature under a high vacuum.

EXAMPLE 11

Side chain-protected [$\beta$-Ala$^{55}$]-eglin C(37–55)-nonapeptide 1.55 g of (8) (approximately 83 $\mu$mol) from Example 10 are stirred for 1.5 hours at room temperature with 20 ml of dichloromethane/acetic acid (9:1 vol.), the resin is filtered off and washed as follows wih 10 ml of solvent each time: 3×dichloromethane, 4×methanol, 4×dichloromethane. The original filtrate is combined with the washing solutions and concentrated in vacuo, approximately 5 ml of acetic acid are added and the whole is lyophilised to dryness yielding the title compound in the form of a colourless powder. HPLC on Nucleosil 5C$_{18}$, 25×4.6 mm, gradient: 100% A/0% B→0% A/100% B for 60 minutes, A=water 0.1% TFA, B=acetonitrile 0.1% TFA, retention time 52 mins. Preparative HPLC: 10 mg are dissolved in 500 $\mu$l of trifluoroethanol/acetonitrile (1:1), separation is carried out with the above gradient and column and the main fraction is collected and concentrated by evaporation. In this manner 6.8 mg of a product are obtained which, according to HPLC, contains more than 90% of the title compound.

EXAMPLE 12

O-[Fmoc-Asp(OBut)-Arg(Mtr)-Gly-Phe-Tyr(But)-Phe-Ser(But)-Arg(Mtr)-Pro-Ala-Ser(But)-Arg(Mtr)-Val-Ser(But)-Arg(Mtr)-Arg(Mtr)-Ser(But)-Arg(Mtr)-Gly]-hydroxy resin (side chain-protected IGF-2 (23–41)-nonadecapeptide bonded to hydroxy resin), (9)

1.20 g of (6) (0.31 mmol) from Example 8 are reacted in a peptide synthesiser with washing processes and Fmoc removal processes analogously to Example 6. All the amino acids are used for the coupling (1 hour) in the form of symmetrical anhydrides (3 equivalents, manufacture as in Example 10). With the amino acids 14, 17 and 18 (that is 36, 39 and 40 of IGF-2) the coupling process is repeated (1 hour). When the synthesis is complete, the resin is washed 3 times with 5 ml of isopropyl alcohol each time and dried under a high vacuum.

EXAMPLE 13

Fmoc-Asp(OBut)-Arg(Mtr)-Gly-Phe-Tyr(But)-Phe-Ser(But)-Arg(Mtr)-Pro-Ala-Ser(But)-Arg(Mtr)-Val-Ser(But)-Arg(Mtr)-Arg(Mtr)-Ser(But)-Arg(Mtr)-Gly-OH [Fmoc-protected IGF-2 (23–41)-nonadecapeptide]

1.65 g of (9) (approximately 154 $\mu$mol) from Example 12 are cleaved with 33 ml of dichloromethane/acetic acid (9:1 vol.) and washed, analogously to Example 11. Lyophilisation yields a colourless powder. For purification, this product is partitioned in an automatic countercurrent partitioning apparatus (5 ml/phase) with a methanol/water/chloroform/carbon tetrachloride mixture (2700:675:900:1575) over 1050 stages. Fractions 46–75 contain the pure title compound (TLC, HPLC) and are together concentrated by evaporation, and the residue is triturated with ether and filtered. According to TLC (4 systems on silica gel) and HPLC (system as in Example 11; retention time 57 mins.) the resulting colourless powder is homogeneous.

FAB-MS (fast atom bombardment mass spectrum): correct mass peak (2480).

EXAMPLE 14

Fmoc-amino resin (10) and amino resin [4-(2,4-dimethoxyphenyl-amino-methyl)-phenoxymethylpolystyrene]

4.1 g of hydroxy resin (3) (approximately 1.89 mmol) are suspended in 80 ml of dioxan. 1.35 g of 9-fluorenylmethylcarbamate (5.65 mmol) (manufactured in accordance with Carpino, L. A. et al., J. Org. Chem. 48, 661 (1983)) and 0.47 ml of 1M benzenesulphonic acid in 1,2-ethane dichloride (EDC) (0.47 mmol) are added and the mixture is maintained at 50° C. for 3 hours. After the addition of a further 0.47 ml of 1M benzenesulphonic acid, the whole is reacted for a further 17 hours at 50° C. The resin is filtered and washed with 30 ml portions of the following solvents: 3×isopropyl alcohol, 3×EDC, 1×dimethylacetamide (DMA), 6×isopropyl alcohol, 3×DMA. The resin is then maintained at room temperature for 2 hours with 5.0 g of benzoic acid anhydride in 25 ml of DMA and 5 ml of pyridine in order to block unreacted hydroxy groups, and washed as described above. The last wash is carried out with 6×isopropyl alcohol. The resulting Fmoc-amino resin (10) is then dried under a high vacuum until a constant mass is reached. After cleaving a sample in accordance with Example 5, the spectrophotometric determination of Fmoc gives a specific loading of approximately 0.35 mmol of Fmoc/g of resin.

In order to produce the free amino resin, 2.0 g of Fmoc-amino resin (10) in 30 ml of 20% piperidine in dimethylacetamide (DMA) are stirred at room temperature for 1 hour, filtered, treated again with a further 30 ml of 20% piperidine in DMA for 1 hour, and washed as follows with 30 ml portions: 3×DMA, 3×isopropyl alcohol, 3×DMA, 6×isopropyl alcohol. The resin is dried under a high vacuum until a constant mass is reached.

EXAMPLE 15

N-[Met-His(Trt)-Glu(OBut)-Gly-Asp(OBut)-Glu(OBut)-Gly-Pro-Gly]-amino resin (11)

0.50 g of Fmoc-amino resin (10) (approximately 175 μmol) from Example 14 are reacted in an automatic peptide synthesiser by means of the following process by successive alternate removal of the Fmoc group and condensing on of Fmoc-Gly, Fmoc-Pro, Fmoc-Gly, Fmoc-Glu(OBut), Fmoc-Asp(OBut), Fmoc-Gly, Fmoc-Glu(OBut), Fmoc-His(Trt) and Fmoc-Met, unreacted amino groups in each instance being blocked by acetylation:

Washing and removal (deblocking) of Fmoc at room temperature with approximately 10 ml each time: 1×isopropyl alcohol (1 min.), 4×DMA degassed (0.5 min.), 6×20% piperidine in DMA (2 mins.), 2×DMA degassed (0.5 min.), 1×isopropyl alcohol (1 min.), 4×DMA degassed (0.5 min.), 3×DMA dist. (0.5 min.).

Coupling: 0.52 mmol of protected amino acid 2,4,5-trichlorophenyl ester and 0.92 ml of 0.57M 1-hydroxybenzotriazole (HOBt)/0.57M diisopropylethylamine in DMA (0.52 mmol) with the addition of 0.88 ml of DMA (30 mins. at room temperature).

Washing and acetylation of the remaining free amino groups with: 1×acetic anhydride/pyridine/DMA (1:1:8 vol.) (5 mins.), 3×DMA degassed (0.5 min.), 1×isopropyl alcohol (1 min.), 3×DMA degassed (0.5 min.). The terinal Fmoc group is removed in the manner described above. The resin is washed with isopropyl alcohol and dried under a high vacuum at room temperature.

EXAMPLE 16

Met-His-Glu-Gly-Asp-Glu-Gly-Pro-Gly-NH$_2$ (MIF-related protein 14 (94–102)-amide 0.65 g of (11) (approximately 150 mmol) from Example 15 are washed in a column for 60 mins. with approximately 30 ml of 2% trifluoroacetic acid (TFA) in dichloromethane, the eluate is concentrated in vacuo to approximately 0.3 ml, 1 l of TFA/water (95:5 vol.) is added and the whole is left at room temperature for 15 mins. for complete removal of the protecting groups. The peptide amide is precipitated by the addition of 5 ml of diisopropyl ether. The precipitate is filtered off and dried in vacuo. The product is dissolved in 5 ml of water, the turbid portion is centrifuged off and the supernatant is lyophilised. A colourless powder is obtained which, according to HPLC, is more than 90% title compound. HPLC: retention time 6.8 mins., Nucleosil column 7C$_{18}$, 120×4.6 mm, gradient: 100% A/0% B→10% A/90% B in 30 1 mins., A=0.1% TFA/water, B=0.1% TFA/acetonitrile, 1.5 ml/min., detection at 215 nm. FAB-MS: mass peak 927 (M+H$^+$).

EXAMPLE 17

O-[Fmoc-Ala-Tyr(But)-Arg(Mtr)-Pro-Ser(But)-Glu(OBut)-Thr(But)-Leu-Cys(Trt)-Gly-Gly-Glu(OBut)-Leu-Val-Asp(OBut)-Thr(But)-Leu-Gln-Phe-Val-Cys(SBut)-Gly]-hydroxy resin (side chain-protected IGF-2 (1–22)-docosapeptide bonded to hydroxy resin), (12)

1.00 g of O-[Fmoc-Gly]-hydroxy resin (6) (approximately 0.36 mmol) are reacted in a peptide synthesiser with washing processes and Fmoc-removal processes analogously to Example 15.

Coupling: Val, Gln, Gly, Leu and Arg are coupled in the form of Fmoc-amino acid 2,4,5-trichlorophenyl ester (0.72 mmol) in 1.20 ml of DMA together with 1.44 ml of 0.5M HOBt/0.5M diisopropylethylamine in DMA at room temperature for 1 hour. The other amino acid derivatives are coupled in the form of symmetrical anhydrides (1.08 mmol) (preparation analogous to Example 10), for 1 hour at room temperature. In the case of amino acids Nos. 3, 8, 10, 11, 18, 20 and 21, the process is repeated (recoupling). When the synthesis is complete, the resin is washed 5 times with isopropyl alcohol, the terminal Fmoc group being retained, and dried under a high vacuum.

EXAMPLE 18

Fmoc-Ala-Tyr(But)-Arg(Mtr)-Pro-Ser(But)-Glu(OBut)-Thr(But)-Leu-Cys(Trt)-Gly-Gly-Glu(OBut)-Leu-Val-Asp(OBut)-Thr(But)-Leu-Gln-Phe-Val-Cys(SBut)-Gly-OH (side chain-protected IGF-2 (1–22)-docosapeptide)

1.80 g of (12) (approximately 0.19 mmol) from Example 17 are mixed for 1.5 hours at room temperature with 35 ml of dichloromethane/acetic acid (9:1 vol.). The resin is filtered off and the difficultly soluble fragment is extracted at 60° C. as follows: 3×50 ml dimethyl sulphoxide (DMSO), 3×trifluoroethanol/dichloromethane (1:1 vol.), 1×N-methylpyrrolidone/DMSO (8:2 vol.). The combined filtrates are concentrated by evaporation under a high vacuum and the residue is stirred for 1 hour at 50° C. with 5 ml of water/methanol (5:95 vol.). The undissolved material is filtered off and dried at room temperature under a high vacuum. The extremely difficultly soluble fragment cannot be analysed by the HPLC technique. TLC (2 systems): the product is more than 90% strength (dissolved in DMSO/N-methylpyrrolidone (2:8)). FAB-MS: mass peak 3539 (M+Na$^+$).

EXAMPLE 19

O-[Fmoc-Ala-Tyr(But)-Arg(Mtr)-Pro-Ser(But)-Glu(OBut)-Thr(But)-Leu-Cys(Trt)-Gly]-hydroxy resin (side chain-protected IGF-2 (1–10)-undecapeptide bonded to hydroxy resin), (13)

1.00 g of O-[Fmoc-Gly]-hydroxy resin (6) (approximately 0.36 mmol) is reacted in a peptide synthesiser with washing processes and Fmoc-removal processes analogously to Example 15.

Coupling: the amino acid derivatives are coupled in the form of symmetrical anhydrides (1.08 mmol) (preparation analogous to Example 10) for 1 hour at room temperature. In the case of amino acids Nos. 3, 8 and 9 the coupling process is repeated with 2 equivalents of 2,4,5-trichlorophenyl ester. When the synthesis is complete the resin is washed 5 times with isopropyl alcohol, the terminal Fmoc group being retained, and dried under a high vacuum.

EXAMPLE 20

Fmoc-Ala-Tyr(But)-Arg(Mtr)-Pro-Ser(But)-Glu(OBut)-Thr(But)-Leu-Cys(Trt)-Gly (side chain-protected IGF-2 (1-10)-undecapeptide)

1.50 g of (13) (approximately 0.19 mmol) from Example 19 are mixed for 1.5 hours at room temperature with 30 ml of dichloromethane/acetic acid (9:1 vol.). The resin is filtered off and the filtrate is concentrated in vacuo and lyophilised under a high vacuum. The resulting colourless powder is for the purposes of purification partitioned in an automatic countercurrent partitioning apparatus (5 ml/phase) with the same mixture as in Example 13 over 1330 stages. Fractions 65-111 contain the pure title compound (TLC, HPLC) and are together concentrated by evaporation. The residue is triturated with ether and filtered. According to TLC (5 systems on silica gel) and HPLC, the colourless powder is homogeneous. Retention time 24.1 mins. on Nucleosil column 5C$_{18}$, 4.6×250 mm, gradient 50% A/50% B→0% A/100% B in 30 mins., A=0.1% TFA/water, B=0.1% TFA/acetonitrile, 1.0 ml/min., detection at 215 nm.

EXAMPLE 21

O-[Asn-Phe-Phe-D-Trp-Lys(Boc)-Thr(But)-Phe-Gaba]-hydroxy resin (side chain-protected somatostatin-D-Trp(8)-4-aminobutyric acid(12)-(5-12)-octapeptide bonded to hydroxy resin), (14)

1.00 g of O-[Fmoc-Gaba]-hydroxy resin (produced analogously to Example 8 with 4-aminobutyric acid instead of glycine) (approximately 0.31 mmol) is reacted in a peptide synthesiser with washing processes and Fmoc-removal processes analogously to Example 15.

Coupling: the amino acid derivatives are coupled in the form of symmetrical anhydrides (0.93 mmol) (preparation analogous to Example 10) for 1 hour at room temperature. Phe and Asn are coupled in the form of 2,4,5-trichlorophenyl ester (2 equivalents). Recoupling is carried out with amino acid 1 (Asn). When the synthesis is complete, and after the terminal Fmoc group has been removed, the resin is washed 5 times with isopropyl alcohol and dried under a high vacuum.

EXAMPLE 22

H-Asn-Phe-Phe-D-Trp-Lys(Boc)-Thr(But)-Phe-Gaba-OH (side chain-protected somatostatin-D-Trp(8)-4-aminobutyric acid(12)-(5-12)-octapeptide)

1.38 g of (14) (approximately 0.26 mmol) from Example 21 are mixed for 1 hour at 50° C. with 5 ml of 5% pyridine hydrochloride in DMA. The resin is filtered off and washed with DMSO, the filtrate is concentrated under a high vacuum and lyophilised once from DMSO and twice from tert.-butyl alcohol. According to HPLC the resulting colourless powder is more than 95% pure and in HPLC and TLC is identical to an authentic specimen that has been produced by synthesis in solution. HPLC: retention time 20.6 mins., Nucleosil column 5C18, 4.6×250 mm, gradient 100% A/0% B→10% A/90% B in 30 mins., A=0.1% TFA/water, B=0.1% TFA/acetonitrile, 1.0 ml/min., detection at 215 nm.

I claim:

1. A synthetic resin based on a polystyrene that can be used as a support for solid phase peptide synthesis and that has been cross-linked with from 0 to 5 mol% of divinyl benzene, characterised in that it has been substituted at benzene rings of its skeletal structure by groups of the formula

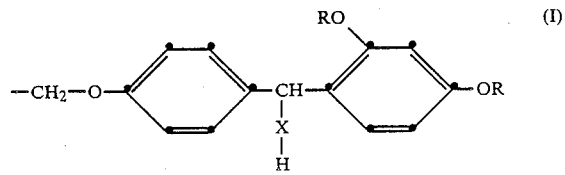

in which X represents —O— or —NH— and R represents C$_1$-C$_4$-alkyl.

2. A synthetic resin according to claim 1 in which the polystyrene is in the form of a copolymer with from 1 to 2 mol% divinyl benzene.

3. A synthetic resin according to claim 2 in which in formula I X represents —O— and R represents methyl.

4. A synthetic resin according to claim 2 in which in formula I X represents —NH— and R represents methyl.

5. A synthetic resin of the structure defined in claim 1, that instead of the —X—H group carries a —N-H—W, —X—AM—W or X—AM—H group in which —X— represents —O— or —NH—, W represents an N-terminal amino-protecting group and AM represents the acyl radical of an amino acid sequence consisting of from 1 to 180 amimo acid residues which is protected or unprotected at functional groups.

6. A synthetic resin according to claim 1 with attached protected or unprotected amino acid, peptide or peptide amide residues.

* * * * *